US011235327B2

(12) United States Patent
Kurkowski et al.

(10) Patent No.: US 11,235,327 B2
(45) Date of Patent: Feb. 1, 2022

(54) POINT OF CARE TEST CARTRIDGE (71) Applicant: EasyDx, Inc., Roseville, MN (US)

(72) Inventors: James D. Kurkowski, Roseville, MN (US); Thomas P. Brastad, Ramsey, MN (US); Martin P. Babcock, White Bear Lake, MN (US); Michael E. Collison, Eagan, MN (US)

(73) Assignee: EasyDx, Inc., Roseville, MN (US)

( * ) Notice: Subject to any disclaimer, the term of this patent is extended or adjusted under 35 U.S.C. 154(b) by 394 days.

(21) Appl. No.: 15/947,357

(22) Filed: Apr. 6, 2018

(65) Prior Publication Data

US 2018/0290139 A1 Oct. 11, 2018

Related U.S. Application Data (60) Provisional application No. 62/482,871, filed on Apr. 7, 2017.

(51) Int. Cl.
B01L 3/00 (2006.01)
G01N 33/487 (2006.01)

(52) U.S. Cl.
CPC ... B01L 3/502746 (2013.01); B01L 3/502715 (2013.01); B01L 3/502761 (2013.01);
(Continued)

(58) Field of Classification Search
None
See application file for complete search history.

(56) References Cited

U.S. PATENT DOCUMENTS 5,064,618 A 11/1991 Baker et al.
5,096,669 A * 3/1992 Lauks ............... B01L 3/502707
204/403.02

(Continued)

FOREIGN PATENT DOCUMENTS

CN 111094992 A 5/2020
CN 113260865 A 8/2021
(Continued)

OTHER PUBLICATIONS

"International Application Serial No. PCT/US2018/026018, International Preliminary Report on Patentability dated Mar. 26, 2019", 10 pgs.

(Continued)

Primary Examiner — Jill A Warden
Assistant Examiner — Brittany I Fisher
(74) Attorney, Agent, or Firm — Schwegman Lundberg & Woessner, P.A.

(57) ABSTRACT

A test cartridge for evaluating biological fluids can have a sensor flow cell defining a flow path for selectively passing a test fluid or biological fluid across a sensor to evaluate the sensor or the biological fluid. The test cartridge can include a sample port and at least one deformable reservoir, both formed as part of the test cartridge and fluidly connected to the flow path upstream of the sensor. A biological fluid can be manually fed into the flow path through the sample port for evaluation by the sensor. Before the biological fluid is fed through the sample port, the deformable reservoir can be manually ruptured to pass the test fluid contained within the reservoir across the sensor to first evaluate the sensor. In an example, the deformable reservoir can include a first reservoir containing a liquid quality control (LQC) fluid and a second reservoir containing a calibration fluid.

12 Claims, 10 Drawing Sheets (52) U.S. Cl.
CPC ..... *B01L 2200/10* (2013.01); *B01L 2200/143* (2013.01); *B01L 2300/044* (2013.01); *B01L 2300/047* (2013.01); *B01L 2300/0663* (2013.01); *B01L 2300/0809* (2013.01); *B01L 2300/0845* (2013.01); *B01L 2300/0867* (2013.01); *B01L 2300/0877* (2013.01); *B01L 2300/0887* (2013.01); *B01L 2400/0481* (2013.01)

(56) References Cited

U.S. PATENT DOCUMENTS

| | | | |
|---|---|---|---|
| 6,037,178 A | 3/2000 | Leiner et al. | |
| 7,090,803 B1* | 8/2006 | Gould | G01N 33/558 422/413 |
| 7,569,393 B2 | 8/2009 | Van Sin et al. | |
| 7,635,594 B2 | 12/2009 | Holmes et al. | |
| 8,105,849 B2 | 1/2012 | Mcdevitt et al. | |
| 8,747,747 B2 | 6/2014 | Hunter | |
| 8,826,752 B2 | 9/2014 | Miller | |
| 9,458,488 B2 | 10/2016 | Johnson et al. | |
| 2002/0094583 A1* | 7/2002 | Seher | B01L 3/50273 436/180 |
| 2003/0224523 A1* | 12/2003 | Thornberg | B01L 3/502738 436/43 |
| 2004/0222091 A1* | 11/2004 | Lauks | B01L 3/502715 204/400 |
| 2006/0108218 A1* | 5/2006 | Gephart | A61B 5/14546 204/400 |
| 2010/0068097 A1* | 3/2010 | Ade | B01L 3/52 422/68.1 |
| 2010/0161267 A1 | 6/2010 | Bartel et al. | |
| 2011/0201099 A1* | 8/2011 | Anderson | G01F 23/292 435/287.2 |
| 2012/0167672 A1* | 7/2012 | Miller | G01N 1/10 73/61.59 |
| 2015/0037786 A1* | 2/2015 | Salsman | G02B 21/16 435/5 |
| 2015/0300957 A1* | 10/2015 | Salsman | B01L 3/502 422/413 |
| 2016/0245793 A1 | 8/2016 | Samsoondar | |
| 2016/0356800 A1 | 12/2016 | Glavina et al. | |
| 2017/0202489 A1 | 7/2017 | Crane et al. | |
| 2018/0119215 A1 | 5/2018 | Esfandyarpour et al. | |
| 2018/0292380 A1 | 10/2018 | Kurkowski et al. | |

FOREIGN PATENT DOCUMENTS

| | | |
|---|---|---|
| JP | 2020513108 A | 4/2020 |
| JP | 2020513218 A | 5/2020 |
| WO | WO-8504719 A1 | 10/1985 |
| WO | WO-9736542 A1 | 10/1997 |
| WO | 2007125468 | 11/2007 |
| WO | WO-2009036429 A2 | 3/2009 |
| WO | WO-2015118313 A1 | 8/2015 |
| WO | 2017165967 | 10/2017 |
| WO | WO-2018187426 A1 | 10/2018 |
| WO | WO-2018187720 A2 | 10/2018 |

OTHER PUBLICATIONS

"International Application Serial No. PCT/US2018/026510, International Preliminary Report on Patentability dated May 7, 2019", 8 pgs.
"U.S. Appl. No. 15/481,698, Restriction Requirement dated Aug. 20, 2019", 6 pgs.
"U.S. Appl. No. 15/481,698, Response filed Oct. 21, 2019 to Restriction Requirement dated Aug. 20, 2019", 7 pgs.
"U.S. Appl. No. 15/481,698, Non Final Office Action dated Jan. 13, 2020", 9 pgs.
"European Application Serial No. 18781599.8, Extended European Search Report dated Feb. 11, 2020", 8 pgs.
"International Application Serial No. PCT/US2018/026018, International Search Report dated Aug. 20, 2018", 5 pgs.
"International Application Serial No. PCT/US2018/026018, Response filed Feb. 7, 2019 to Written Opinion dated Aug. 20, 2018", 18 pgs.
"International Application Serial No. PCT/US2018/026018, Written Opinion dated Aug. 20, 2018", 7 pgs.
"International Application Serial No. PCT/US2018/026510, International Search Report dated Dec. 4, 2018", 3 pgs.
"International Application Serial No. PCT/US2018/026510, Response filed Mar. 4, 2019 to Written Opinion dated Dec. 4, 2018", 16 pgs.
"International Application Serial No. PCT/US2018/026510, Written Opinion dated Dec. 4, 2018", 10 pgs.
"U.S. Appl. No. 15/481,698, Final Office Action dated Jul. 1, 2020", 8 pgs.
"U.S. Appl. No. 15/481,698, Response filed Apr. 13, 2020 to Non Final Office Action dated Jan. 13, 2020", 10 pgs.
"U.S. Appl. No. 15/481,698, Response filed Dec. 30, 2020 to Final Office Action dated Jul. 1, 2020", 14 pgs.
"European Application Serial No. 18781599.8, Response filed Sep. 9, 2020 to Extended European Search Report dated Feb. 11, 2020", 31 pgs.
"European Application Serial No. 18781601.2, Extended European Search Report dated Apr. 22, 2020", 10 pgs.
"European Application Serial No. 18781601.2, Response filed Nov. 23, 2020 to Extended European Search Report dated Apr. 22, 2020", 27 pgs.
"Chinese Application Serial No. 201880038255.3, Office Action dated Mar. 22, 2021", W out English translation, 1 pgs.
"European Application Serial No. 18781601.2, Communication Pursuant to Article 94(3) EPC dated Mar. 22, 2021", 4 pgs.
"U.S. Appl. No. 15/481,698, Non Final Office Action dated Feb. 5, 2021", 12 pgs.
"U.S. Appl. No. 15/481,698, Response filed May 5, 2021 to Non Final Office Action dated Feb. 5, 2021", 15 pgs.
"U.S. Appl. No. 15/481,698, Final Office Action dated Jul. 15, 2021", 13 pgs.
"European Application Serial No. 18781601.2, Response filed Jun. 30, 2021 to Communication Pursuant to Article 94(3) EPC dated Mar. 22, 2021", 18 pgs.
U.S. Appl. No. 15/481,698, filed Apr. 7, 2017, Multi-Liquid Quality Calibration Single-Use Cartridge.

* cited by examiner

POINT OF CARE TEST CARTRIDGE

PRIORITY

This application claims the benefit of priority of U.S. Provisional Application Ser. No. 62/482,871, filed on Apr. 7, 2017, and which is incorporated by reference herein in its entirety.

TECHNICAL FIELD

This document pertains generally, but not by way of limitation, to test cartridges containing onboard fluids for the testing of a biological fluid.

BACKGROUND

Point of care ("POC") testing devices are used to evaluate collected biological samples immediately following collection of the samples. POC testing devices can have reusable sensors or can be configured to receive cartridges having single use sensors, wherein biological samples can be fed into the testing device or removable cartridge to evaluate the biological sample.

Governmental regulation or hospital procedures often require that POC testing devices are tested at regular intervals (e.g. at the beginning of each shift or prior to each evaluation of each biological sample) by testing known samples to confirm the system is accurately measuring samples. Liquid quality control ("LQC") fluids formulated to provide known sensor measurement of at least one analyte is administered to the POC device. The sensors can take measurements of the LQC fluid and compare the measurements of the analyte provided by the single use sensors to the expected known measurements for the LQC fluid. Typically, multiple aliquots of a plurality of LQC fluids, each having different known analyte concentrations, are tested to determine if the sensors are operating properly and accurately.

An inherent drawback is that administering each aliquot of LQC fluid is costly and time-consuming. The required time to administer LQC fluid to perform each evaluation test can reduce the effective time each POC device can be used to make actual measurements for biological samples. In addition, each evaluation cycle can consume a single use sensor cartridge requiring use of a fresh sensor cartridge to test a biological sample.

OVERVIEW

The present inventors have recognized, among other things, that a problem to be solved can include inefficient LQC testing of the measurement systems of POC devices. In an example, the present subject matter can provide a solution to this problem such as by a test cartridge having a sensor flow cell defining a flow path for selectively passing a LQC fluid or a biological fluid across the sensor to evaluate the quality and/or operation of the sensor or evaluate the biological fluid. The test cartridge can include a sample port and at least one deformable reservoir, each fluidly connected to the flow path upstream of the sensor. The deformable reservoir can contain an aliquot of LQC fluid, calibration fluid, or other test fluid for evaluating or calibrating the sensor. A biological fluid can be manually fed into the flow path through the sample port for evaluation by the sensor.

In an example, the test cartridge can include at least two deformable reservoirs, each deformable reservoir can contain a test fluid such as a calibration fluid or a LQC fluid. In an example, the deformable reservoirs can be part of the cartridge (as opposed to being removably attached to the cartridge). In an example having two deformable reservoirs, the first deformable reservoir can be manually deformed to rupture the reservoir and force a first test fluid through the flow path and over the sensor. The second deformable reservoir can be manually ruptured to displace the first test fluid and pass a second test fluid across the sensor to evaluate the quality or operation of the sensor. The user can visually see when one or both of the deformable reservoirs have been ruptured. In an example, the first test fluid can comprise a calibration fluid for calibrating the sensor and the second test fluid can comprise an LQC fluid for evaluating operation of the sensor. In another example, the first test fluid can comprise a first LQC fluid and the second test fluid can comprise a second LQC fluid. The biological fluid can be then manually loaded through the sample port to displace the second LQC fluid and evaluate the biological fluid with the calibrated sensor. The sample port for receiving the biological fluid can be separate and distinct from the one or more reservoirs. Test cartridges that contain an LQC fluid within a deformable reservoir that is part of the test cartridge can facilitate on-board LQC testing. In other words, LQC testing can be provided to the user with the test cartridge.

Each reservoir of the test cartridge can be manually deformed in order to rupture the reservoir. Because the reservoir can be manually depressed, a reader (also referred to an instrument) used in conjunction with the test cartridge also does not require any moving parts for operation of the instrument.

In an example, the test cartridge can include only one deformable reservoir. The test cartridge having a single reservoir can operate like the test cartridge described above having first and second deformable reservoirs, but the single reservoir cartridge has one test fluid used prior to the biological fluid, instead of two test fluids in the dual reservoir design.

This overview is intended to provide an overview of subject matter of the present patent application. It is not intended to provide an exclusive or exhaustive explanation of the present subject matter. The detailed description is included to provide further information about the present patent application.

BRIEF DESCRIPTION OF THE DRAWINGS

In the drawings, which are not necessarily drawn to scale, like numerals may describe similar components in different views. Like numerals having different letter suffixes may represent different instances of similar components. The drawings illustrate generally, by way of example, but not by way of limitation, various embodiments discussed in the present document.

DETAILED DESCRIPTION

Figure 1:
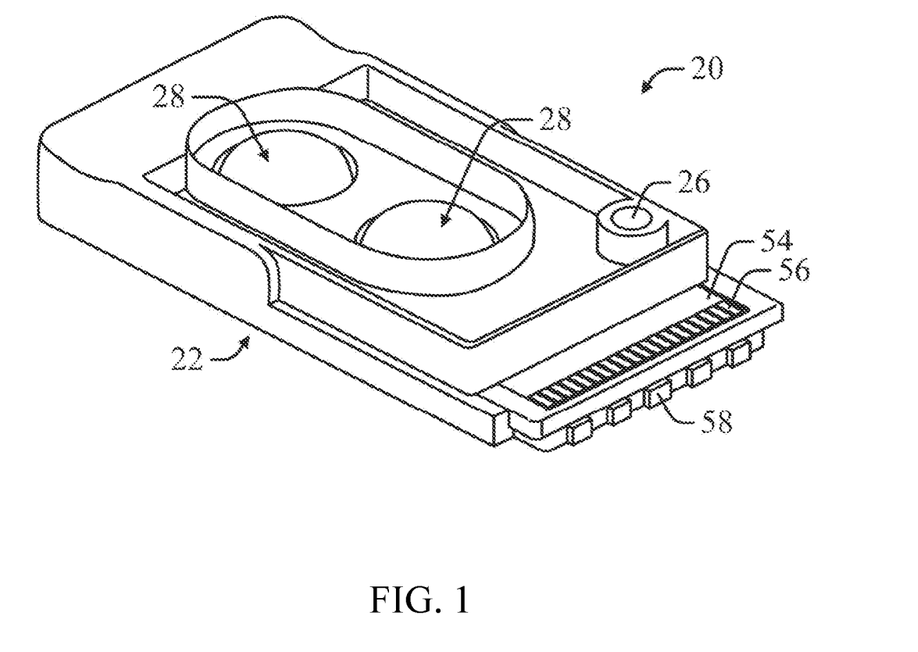
FIG. 1 is a perspective view of a test cartridge according to an example of the present disclosure.
Figure 2:
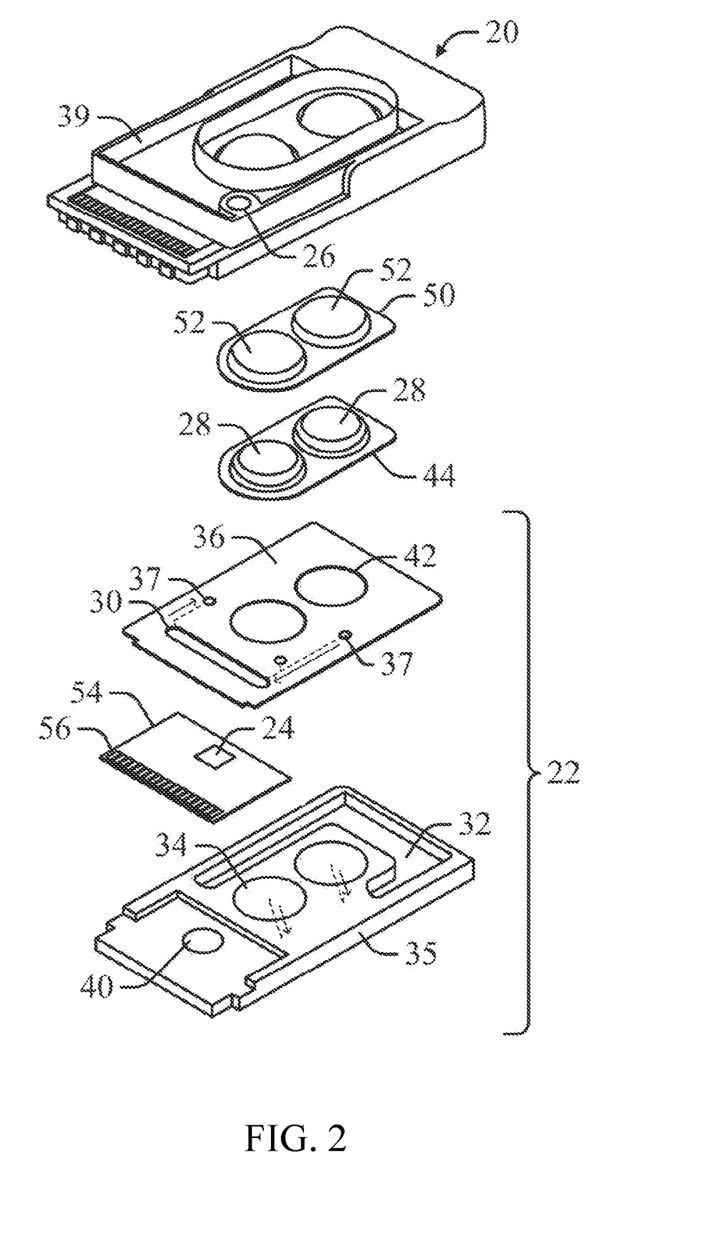
FIG. 2 is an exploded perspective view of a test cartridge according to an example of the present disclosure.

As depicted in FIGS. 1 and 2, a test cartridge 20, according to an example of the present disclosure, can include a sensor flow cell 22 defining a flow path for passing a test fluid or a biological fluid across a sensor 24 for evaluation of the test fluid or biological fluid with the sensor 24. The test fluid, as described herein, can comprise an LQC fluid for evaluating operation of the sensor 24 or a calibration fluid for calibrating the sensor 24. The test cartridge 20 can include a sample port 26 fluidly connected to the flow path upstream of the sensor 24 such that a biological fluid can be fed into the flow path and over the sensor 24. A deformable reservoir 28 containing an aliquot of a test fluid can be fluidly connected to the flow path upstream of the sensor 24 and upstream of the sample port 26. The deformable reservoir 28 can be manually deformed to rupture the deformable reservoir 28 and force the aliquot of test fluid through the flow path and over the sensor 24. The deformable reservoir 28 can be part of the test cartridge 20 or contained therein, rather than being removably attached to the test cartridge 20. The deformable reservoir 28 can be separate and distinct from the sample port 26.

In an example, in operation, the deformable reservoir 28 can be manually deformed to push the aliquot of test fluid over the sensor 24 for evaluation by the sensor 24. The deformable reservoir 28 can comprise an LQC fluid that is measured by the sensor 24 to evaluate operation of the sensor 24 prior to, subsequent to, or without calibration of the sensor 24. In certain examples, a storage fluid can be initially stored over the sensor 24 for transport and storage of the test cartridge 20 and displaced from the LQC fluid pushed from the deformable reservoir 28. In this configuration, the storage fluid can comprise a calibration fluid that is evaluated by the sensor 24 to determine if a correction to the sensor 24 measurements is required and the offset required to calibrate the sensor 24. Upon confirmation of a properly functioning sensor 24, a biological fluid can then be fed through the sample port 26 to displace the LQC fluid over the sensor 24 such that the calibrated sensor 24 can evaluate the biological fluid. In at least one example, the biological fluid can be fed through the sample port 26 and across the sensor 24 without pushing LQC fluid across the sensor 24.

As depicted in FIGS. 2, 5, and 6A-C, in an example, the sensor flow cell 22 can define a flow path extending at least from a testing chamber 30 to a waste chamber 32. In an example, the sensor flow cell 22 can comprise a base plate 35 and a cover plate 36 that cooperate to define at least a portion of the flow path. As depicted in FIG. 2, the cover plate 36 can define the testing chamber 30, wherein the sensor 24 can be positioned to align with or otherwise fluidly connected to the testing chamber 30 to evaluate fluids within the testing chamber 30. The waste chamber 32 can be positioned downstream of the testing chamber 30 such that fluid dispelled from the testing chamber 30 is pushed along the flow path into the waste chamber 32. A cover portion of the test cartridge 20 that is aligned with the waste chamber 32 can include an air vent 33 (see FIG. 5). As depicted in FIG. 2, the waster chamber 32 can be defined in the base plate 35. In operation, a first fluid (e.g. storage fluid, calibration fluid) within the testing chamber 30 can be pushed from the testing chamber 30 by a second fluid (e.g. calibration fluid, biological fluid) administered to the flow path upstream of the testing chamber 30.

As illustrated in FIG. 2, in an example, the cover plate 36 can define at least one port 37 permitting fluid to pass through the cover plate 36. The sensor flow cell 22 can comprise a top cover 39 configured to cooperate with the cover plate 36 to define at least portion of the flow path above the cover plate 36.

As depicted in FIG. 2, in an example, the top cover 39 can define the sample port 26. The sample port 26 can be fluidly connected to the flow path upstream of the testing chamber 30 such that providing biological or other fluids through the sample port 26 moves the added fluid into the testing chamber 30 for evaluation with the sensor 24. In an example, the sample port 26 can comprise a luer port configured to engage with a syringe. A nozzle or needle of a fluid filled syringe can be coupled to the luer port, whereby manually depressing the syringe forces the contained fluid (e.g. biological fluid) into the flow path. The fluid pressure generated by expelling fluid from the syringe pushes fluid through the test cartridge 20 without a pump or other mechanical mechanism for moving the fluid. In an example, a cap can be coupled to the sample port 26 to close the sample port 26 when not being used.

As depicted in FIG. 2, in an example, the base plate 35 can define at least one reservoir chamber 34 over which a corresponding reservoir 28 can be positioned for capturing test fluid released from a ruptured reservoir 28. The base plate 35 can comprise a piercing element 41 or other structure for rupturing the reservoir 28. As depicted in FIGS. 5 and 6A-C, each reservoir chamber 34 can be fluidly connected to the flow path upstream of the testing chamber 30 such that the received LQC fluid flows from the reservoir chamber 34 into the testing chamber 30 for evaluation of the fluid with the sensor 24.

As depicted in FIG. 2, the cover plate 36 can include a reservoir port 42 through which the reservoir 28 can be inserted. The cover plate 36 can engage the edges of the reservoir 28 to retain the reservoir 28 over the reservoir chamber 34.

As depicted in FIG. 2, in an example, the test cartridge 20 can include a reservoir cartridge 44 including a plurality of deformable reservoirs 28. The reservoir cartridge 44 can be positioned on the sensor flow cell 22 such that each deformable reservoir 28 aligns with a corresponding reservoir chamber 34. In this configuration, the deformable reservoir 28 can be manually deformed to rupture the deformable reservoir 28 and push the test fluid (e.g. calibration fluid) within the deformable reservoir 28 into the reservoir chamber 34 and into the flow path upstream of the testing chamber 30. The fluid pressure generated by expelling fluid from the deformable reservoir 28 pushes fluid through the test cartridge 20 without a pump or other mechanical mechanism for moving the fluid.

Figure 3:
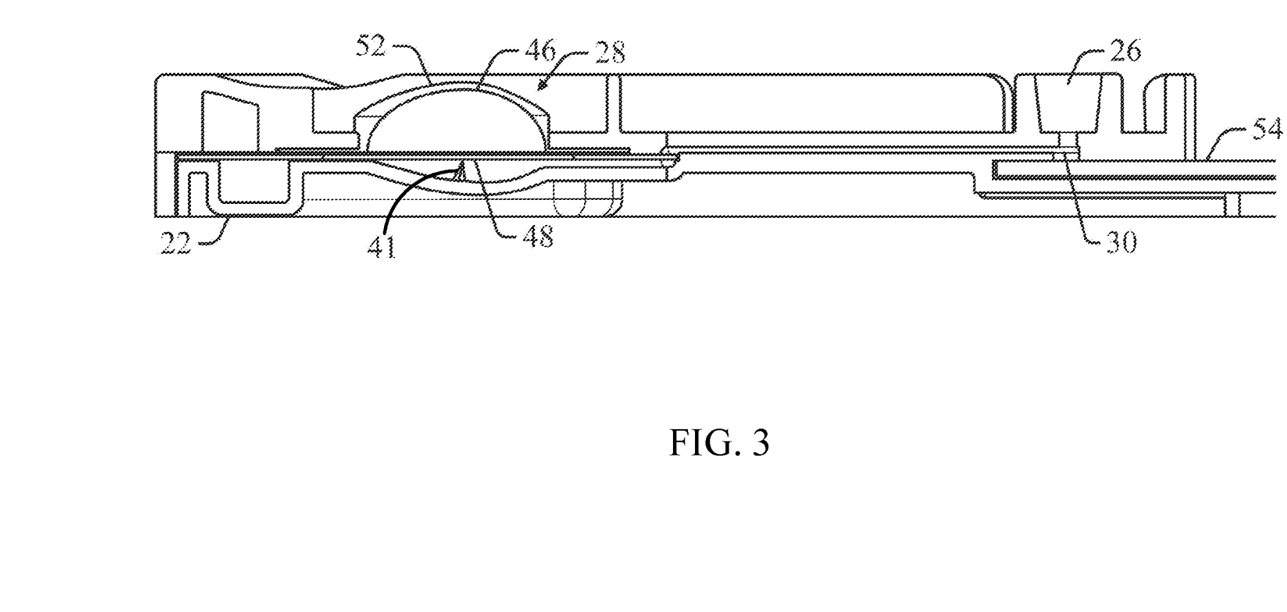
FIG. 3 is a side cross-sectional view of a test cartridge according to an example of the present disclosure.

As illustrated in FIG. 3, in an example, the reservoir cartridge 44 can include a deformable panel 46 and a foil panel 48. The deformable panel 46 can be shaped to include at least one blister defining a space for receiving a fluid. The foil panel 48 can be arranged to enclose a portion of the space defined by each blister to form the deformable reservoir 28. The reservoir cartridge 44 can be positioned on the flow cell 22 such that the foil panel 48 is oriented toward the reservoir chamber 34. In operation, manual pressure can be applied to the blister such that the fluid pressure of the fluid within the space defined by the blister ruptures the foil panel 48. In an example, the sensor flow cell 22 can include the piercing element 41 positioned within the reservoir chamber 34. In this configuration, applying manual pressure to the blister presses a corresponding portion of the foil panel 48 against the piercing element 41 to facilitate rupture of the deformable reservoir 28. In an example, the deformable panel 46 can deflect inward to push the fluid from the reservoir 28 and into the flow path. The foil panel 48 is shown in FIG. 3 as having a generally flat or planar structure; however, it is noted that the foil panel 48 can have a curved-shape.

As depicted in FIG. 2, the test cartridge 20 can include a deformable cover 50 comprising a plurality of reservoir covers 52 positioned on the reservoir cover 50 to align with a deformable reservoir 28. In an example, each reservoir cover 52 can deform when the reservoir cover 52 is depressed to correspondingly deform and rupture the underlying deformable reservoir 28.

Figure 7:
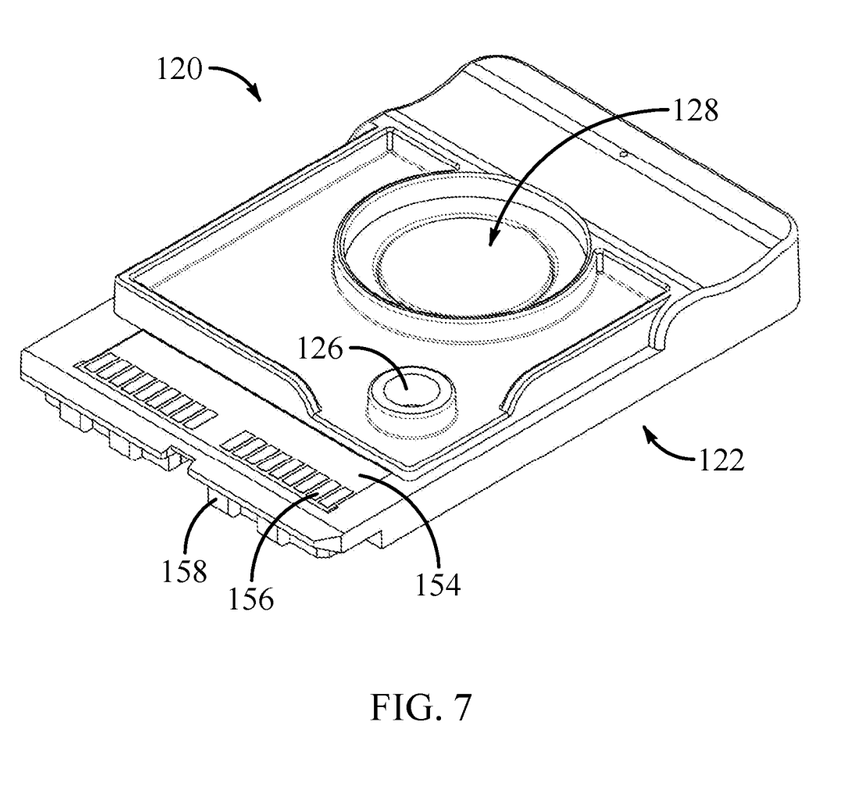
FIG. 7 is a perspective view of another test cartridge according to an example of the present disclosure.

As depicted in FIG. 2, the test cartridge 20 can include a test chip 54 comprising at least one sensor 24 and at least one reader contact 56. The test chip 54 can be positioned on the sensor flow cell 22 such that the at least one sensor 24 aligns with the testing chamber 30. A portion of the test chip 54 extends from the sensor flow cell 22 to expose the reader contacts 56. In this configuration, the test cartridge 20 can be inserted into a reader (or instrument) such that the corresponding contacts of the reader interface with the reader contacts 56. The information gathered by the sensors 24 can be transmitted to the reader through the reader contacts 56, where the information is gathered and evaluated. In at least one example, the test cartridge 20 can include at least one alignment feature 58 for aligning the reader contacts 56 with the corresponding contacts of the reader. An example of the reader/instrument is shown in FIG. 7 and described below.

As depicted in FIG. 2, in an example, the base plate 35 can comprise a heating port 40. A temperature sensor and/or heating element can be positioned within the heating port 40 to monitor and/or alter the heat within the testing chamber 30.

Figure 4A:
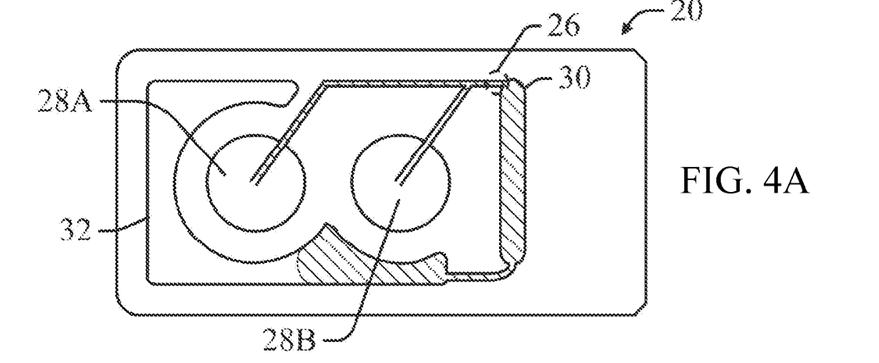
FIG. 4A is a schematic top view of a test cartridge illustrating release of a first LQC fluid from a first reservoir according to an example of the present disclosure.
Figure 4B:
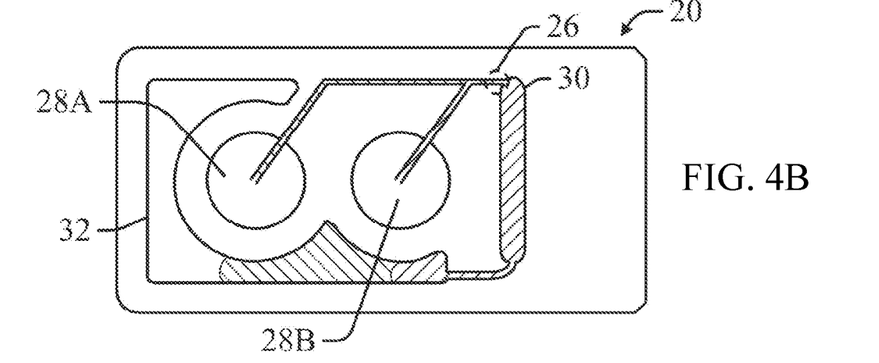
FIG. 4B is a schematic view of the test cartridge depicted in FIG. 4A illustrating release of a second LQC fluid from a second reservoir to displace the first LQC fluid according to an example of the present disclosure.
Figure 4C:
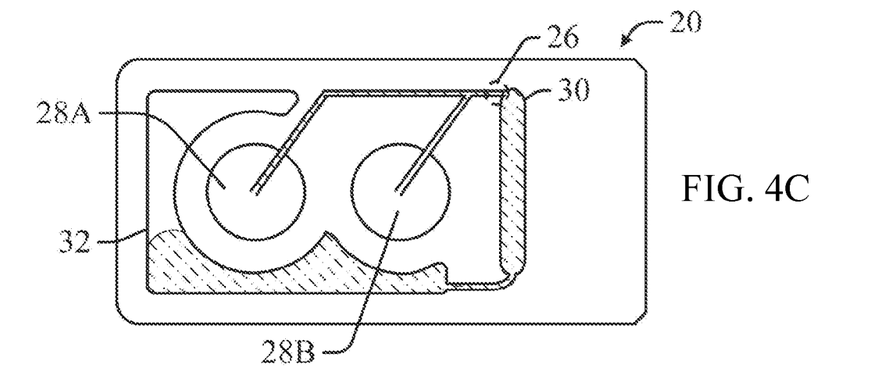
FIG. 4C is a schematic view of the test cartridge depicted in FIG. 4A illustrating injection of a biological fluid into the testing chamber to displace the second LQC fluid according to an example of the present disclosure.
Figure 5:
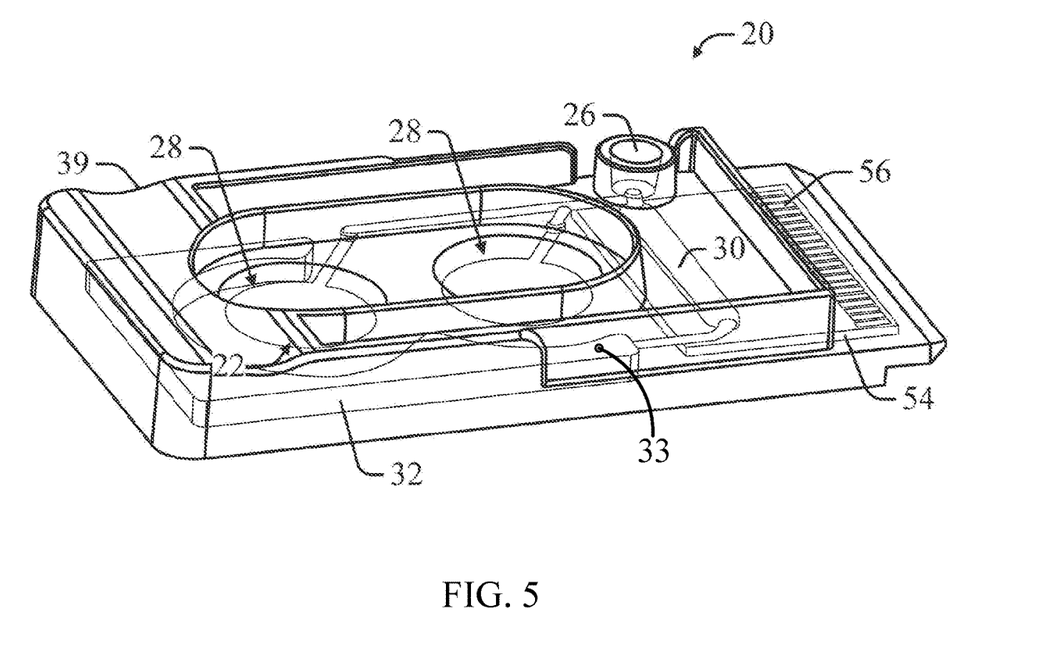
FIG. 5 is a perspective view of a test cartridge having a ghosted top cover to illustrate a flow path according to an example of the present disclosure.
Figure 6A:
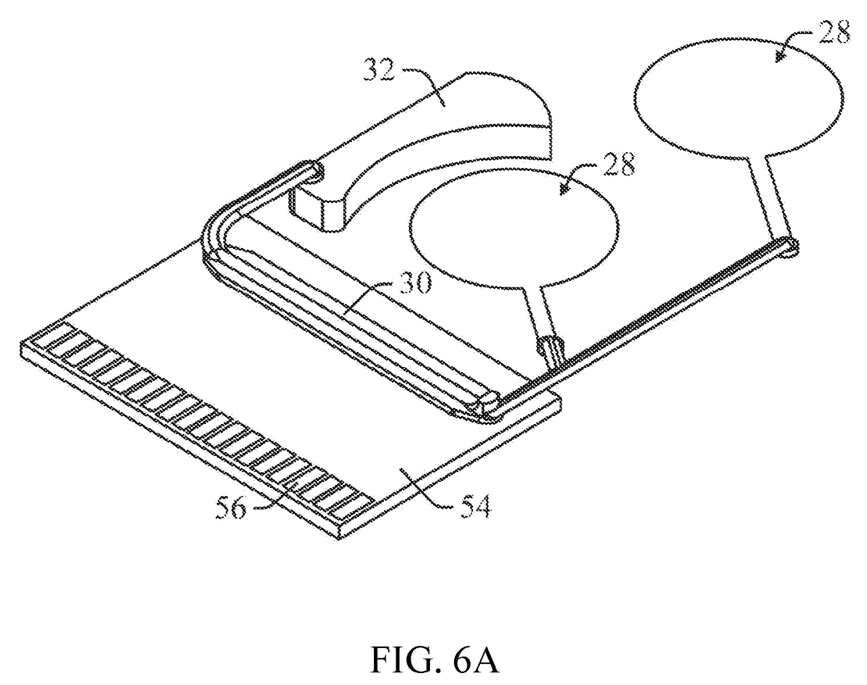
FIG. 6A is a front, top schematic perspective view of a flow path of a test cartridge according to an example of the present disclosure.
Figure 6B:
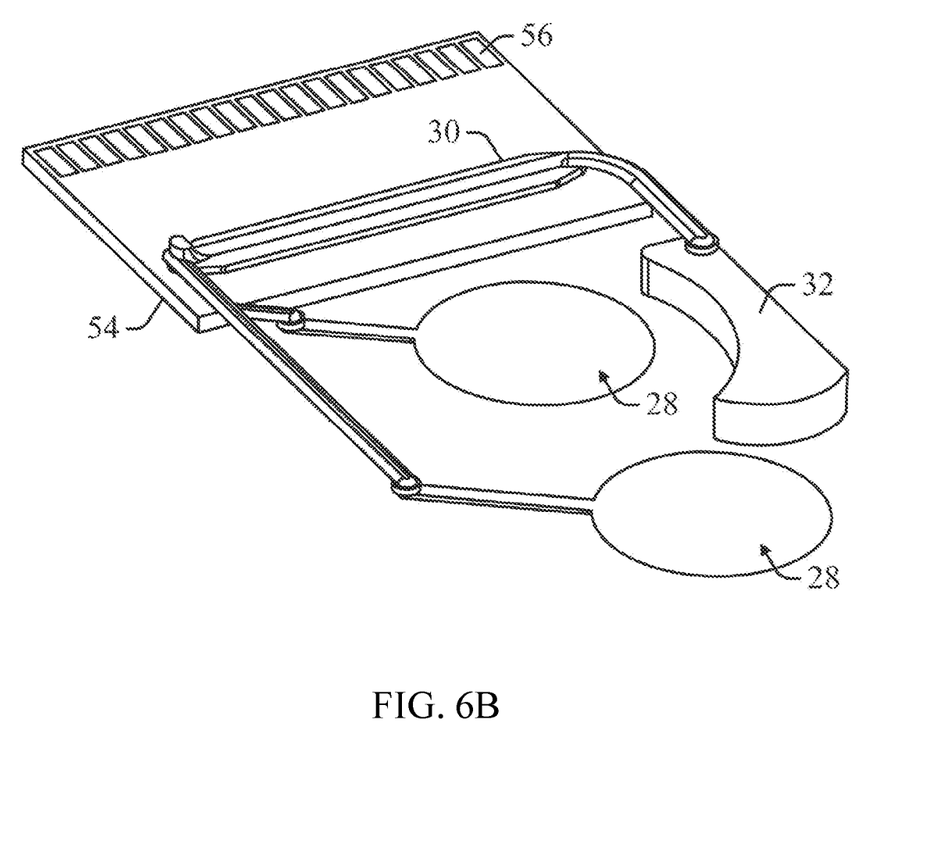
FIG. 6B is a rear, top schematic perspective view of a flow path of a test cartridge according to an example of the present disclosure.
Figure 6C:
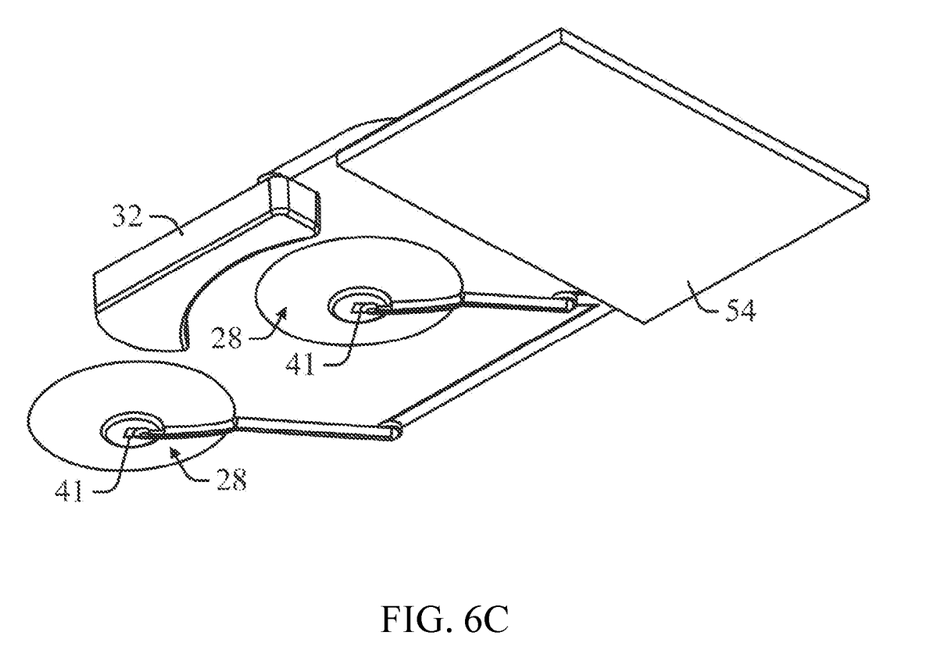
FIG. 6C is a front, bottom schematic perspective view of a flow path of a test cartridge according to an example of the present disclosure.

As illustrated in FIGS. 4A-C, the test cartridge 20 can have a first reservoir 28A and a second reservoir 28B fluidly connected to the flow path in a serial configuration. The first reservoir 28A can contain a first test fluid, while the second reservoir 28B can contain a second test fluid. In an example, the first test fluid can comprise a calibration fluid for calibrating the sensor and the second test fluid can comprise an LQC fluid for evaluating operation of the sensor. In another example, the first test fluid can comprise a first LQC fluid and the second test fluid can comprise a second LQC fluid.

As illustrated in FIG. 4A, the first reservoir 28A can be manually depressed to rupture the first reservoir 28A and push the first test fluid into the flow path and into the testing chamber 30. The sensor 24 can evaluate the first test fluid to calibrate or determine a parameter of the operation of the sensor 24. In an example, the flow path and the testing chamber 30 can be dry or prefilled with a storage fluid for transport and storage of the test cartridge 20. The first reservoir 28A can be sized such that the quantity of first test fluid pushed from the first reservoir 28B is sufficient to completely displace the storage fluid from the testing chamber 30.

As illustrated in FIG. 4B, the second reservoir 28B can be manually depressed to rupture the second reservoir 28B and push the second test fluid into the flow path and into the testing chamber 30. The second test fluid can push the first test fluid from the testing chamber 30 and into the waste chamber 32. The second reservoir 28B can be sized such that the quantity of second test fluid pushed from the second reservoir 28B is sufficient to completely displace the first test fluid from the testing chamber 30. The sensor 24 can evaluate the second test fluid to calibrate or determine a parameter of the operation of the sensor 24.

As illustrated in FIG. 4C, a syringe containing a biological fluid can be connected to the sample port 26, wherein the syringe plunger is depressed to push the biological fluid from the syringe and into the flow path and the testing chamber 30. The syringe can be sized such that the barrel of the syringe can contain sufficient biological fluid such that the quantity of biological fluid pushed from the syringe is sufficient to completely displace the second test fluid from the testing chamber 30.

In an example, the first reservoir 28A can be manually depressed first to push the first test fluid into the testing chamber 30. Alternatively, the second reservoir 28B can be manually depressed first (before the first reservoir 28A) to push the second test fluid into the testing chamber 30 instead of the first test fluid. In this configuration, the user can select the test fluid used or alter the sequence of test fluids used to evaluate or calibrate the sensor 24. The user can visually tell when one or both of the first and second reservoirs 28A, 28B have been depressed and ruptured. Moreover, the reservoirs 28A, 28B and the test cartridge 20 overall, are designed such that a ruptured reservoir remains deformed and liquids from either another reservoir or an injected sample cannot flow into the ruptured reservoir.

In an example, multiple test cartridges 20 can be provided to a user and the test cartridges can contain LQC test fluids at varying levels for a particular component being tested. For example, a first test cartridge can include an LQC test fluid (in one of the deformable reservoirs) with the component at a low level, a second test cartridge can include an LQC test fluid with the component at a middle level, and a third test cartridge can include an LQC test fluid with the component at a high level. Thus, the LQC fluids contained in the test cartridges can be different.

FIG. 7 depicts a test cartridge 120, according to an example of the present disclosure, which can be similar to the test cartridge 20, but can have a single deformable reservoir 28, as compared to the two deformable reservoirs 28 of the test cartridge 20. The test cartridge 120 can include a sensor flow cell 122 defining a flow path for passing a test fluid or a biological fluid across a sensor for evaluation of the test fluid or biological fluid with the sensor. The test cartridge 120 can include a sample port 126 fluidly connected to the flow path upstream of the sensor 124.

A functionality and operation of the test cartridge 120 can be similar to that described above for the test cartridge 20. The deformable reservoir 128 can contain an aliquot of a test fluid and can be fluidly connected to the flow path of the sensor upstream of the sensor and upstream of the sample port 126. The deformable reservoir 128 can be manually deformed to rupture the deformable reservoir 128 and force the aliquot of test fluid through the flow path and over the sensor. The deformable reservoir 128 can be contained within the test cartridge 120 and can be separate from the sample port 126. Because only one reservoir 128 is included in the test cartridge 120, the test cartridge 120 holds one test fluid as compared to the test cartridge 20 which can hold two test fluids. In an example, the test fluid in the deformable reservoir 128 can be a calibration fluid for calibrating the sensor.

Once the deformable reservoir 128 is ruptured, the test fluid can flow through the test cartridge as described above in reference to the test cartridge 20. A biological fluid can then be fed through the sample port 126 to displace the test fluid over the sensor such that the sensor can evaluate the biological fluid. The test cartridge 120 can include a test chip 154, at least one reader contact 156 and at least one alignment feature 158, and such components can function similar to the corresponding component described above for the test cartridge 20. Because the reservoir 128 can be manually depressed, the test cartridge 120 can be used with a reader or instrument that does not include any moving parts to rupture the reservoir. The user can visually see once the deformable reservoir 128 has been ruptured.

Figure 8:
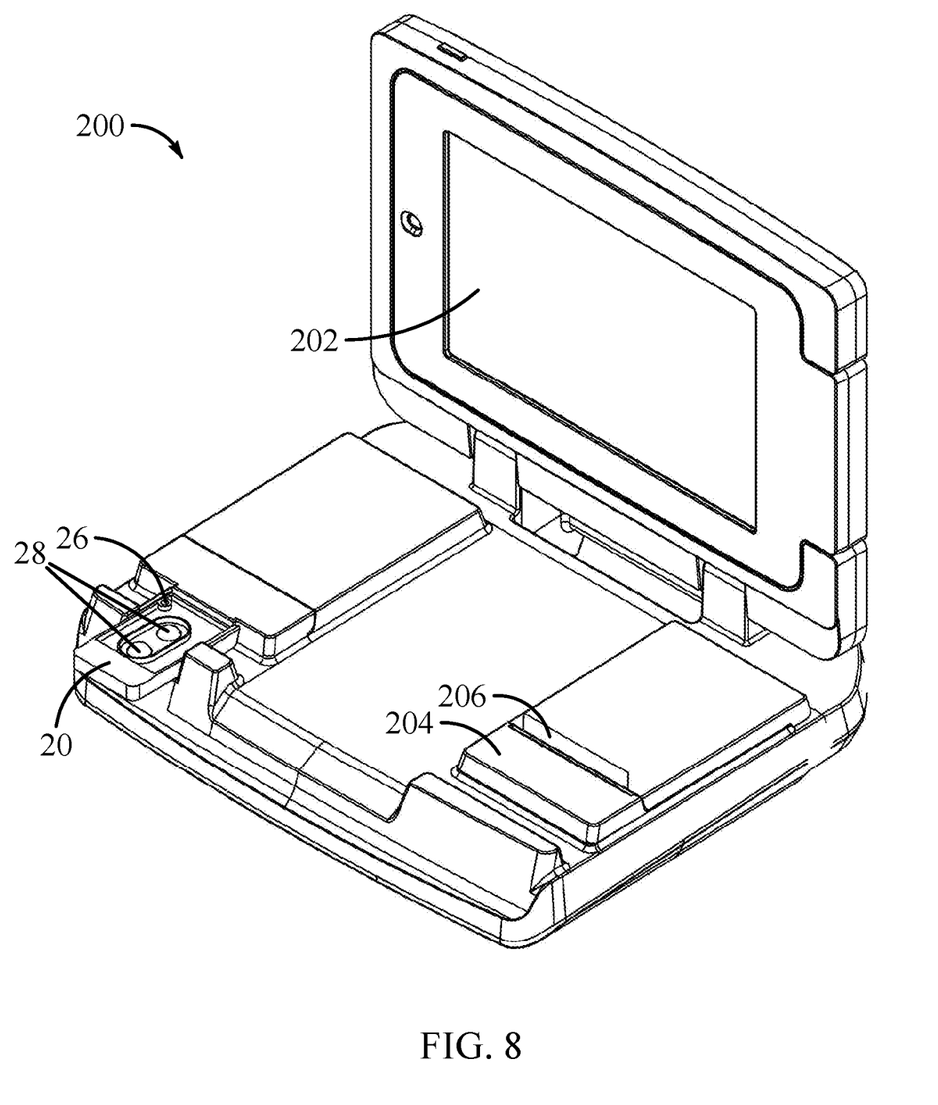
FIG. 8 is a perspective view of a reader or instrument in combination with the test cartridge of FIG. 1.

FIG. 8 depicts a reader 200 (also referred to as an instrument 200) with the test cartridge 20 inserted therein. The end of the test cartridge 20 that has the at least one reader contact 56 and at least one alignment feature 58 can be inserted into the reader 200. The reader 200 can analyze the test fluids stored in the one or more deformable reservoirs 28 of the test cartridge 20. The reader 200 can analyze a biological sample inserted into the test cartridge (from a syringe) through the sample port 26. The reader 200 can include, among other things, a user display screen 202 and an on-board printer 204 for providing a print-out 206 to the user. The reader 200 can be designed for portability or as a stationary instrument.

VARIOUS NOTES & EXAMPLES

Example 1 is a test cartridge for evaluating a fluid, comprising: a sensor flow cell defining a testing chamber and a flow path for passing fluid through the testing chamber; a sensor positionable within the testing chamber and configured to evaluate fluid within the testing chamber; a sample port fluidly connected to the flow path upstream of the testing chamber and configured to receive a biological fluid into the testing chamber through the flow path; and at least one deformable reservoir contained in the cartridge and separate from the sample port, the at least one deformable reservoir fluidly connected to the flow path upstream of the sample port, wherein manually deforming each deformable reservoir of the at least one deformable reservoir ruptures the deformable reservoir to release a test fluid into the testing chamber.

In Example 2, the subject matter of Example 1 optionally includes wherein the testing chamber initially contains a storage fluid over the sensor; wherein at least one of the biological fluid and test fluid displaces the storage fluid.

In Example 3, the subject matter of any one or more of Examples 1-2 optionally include wherein the test fluid comprises at least one of a liquid quality control fluid for evaluating the sensor and a calibration fluid for calibrating the sensor.

In Example 4, the subject matter of Example 3 optionally includes wherein the at least one deformable reservoir comprises: a first deformable reservoir fluidly connected to the flow path upstream of the testing chamber, the first deformable reservoir containing a first liquid control fluid; and a second deformable reservoir fluidly connected to the flow path upstream of the testing chamber, the second deformable reservoir containing a second liquid control fluid; wherein the first and second deformable reservoirs are configured to be sequentially deformed to release the first liquid control and the second liquid control into the testing chamber.

In Example 5, the subject matter of any one or more of Examples 1-2 optionally include wherein the at least one deformable reservoir is a single deformable reservoir containing a calibration fluid for calibrating the sensor.

In Example 6, the subject matter of any one or more of Examples 1-5 optionally include a reservoir cartridge including a deformable panel and a foil panel, the deformable panel being shaped to form a blister to define a space for receiving the test fluid, the foil panel is positionable against the deformable panel to enclose the space and define the deformable reservoir; wherein manually pressing the blister causes fluid pressure against the foil panel to rupture the foil panel and release the test fluid into the flow path.

In Example 7, the subject matter of Example 6 optionally includes a deformable cover comprising at least one reservoir cover, each reservoir cover configured to fit over the deformable reservoir; wherein depressing the reservoir cover deforms and ruptures the deformable reservoir.

In Example 8, the subject matter of any one or more of Examples 1-7 optionally include wherein the sample port is configured to interface with a nozzle of a syringe, the syringe comprising a plunger receivable within a cylinder for receiving biological fluid; wherein depressing the plunger pushes biological fluid into the sample port and through the fluid path.

In Example 9, the subject matter of any one or more of Examples 1-8 optionally include wherein the sensor flow cell defines a waste chamber fluidly connected to the flow path downstream of the testing chamber; wherein fluids displaced from the testing chamber are pushed into the waste chamber.

In Example 10, the subject matter of any one or more of Examples 1-9 optionally include a test chip comprising the sensor and at least one reader contact, and the test cartridge is configured to be inserted into a reader such that the reader contacts interface with corresponding contacts of the reader.

Example 11 is a test system for evaluating a fluid, comprising: a test cartridge, comprising: a sensor flow cell defining a testing chamber and a flow path for passing fluid through the testing chamber, a sensor positionable within the testing chamber and configured to evaluate fluid within the testing chamber, a sample port fluidly connected to the flow path upstream of the testing chamber and configured to receive a biological fluid into the testing chamber through the flow path, and at least one deformable reservoir contained in the test cartridge and separate from the sample port, the at least one deformable reservoir fluidly connected to the flow path upstream of the testing chamber, wherein manually deforming each deformable reservoir ruptures the deformable reservoir to release a test fluid into the testing chamber; and a reader configured to interface with the test cartridge to receive sensor information from the sensor.

In Example 12, the subject matter of Example 11 optionally includes wherein the testing chamber initially contains a storage fluid protecting the sensor; wherein at least one of the biological fluid and test fluid displaces the storage fluid.

In Example 13, the subject matter of any one or more of Examples 11-12 optionally include wherein the test fluid comprises at least one of a liquid quality control fluid for evaluating the sensor and a calibration fluid for calibrating the sensor.

In Example 14, the subject matter of Example 13 optionally includes wherein the at least one deformable reservoir comprises: a first deformable reservoir fluidly connected to the flow path upstream of the testing chamber, the first deformable reservoir containing a first test fluid; and a second deformable reservoir fluidly connected to the flow path upstream of the testing chamber, the second deformable reservoir containing a second test fluid; wherein the first and second deformable reservoirs are configured to be sequentially deformed to release the first test fluid and the second test fluid into the testing chamber.

In Example 15, the subject matter of any one or more of Examples 11-14 optionally include wherein the test cartridge further comprises: a reservoir cartridge including a deformable panel and a foil panel, the deformable panel being shaped to form a blister to define a space for receiving the test fluid, the foil panel is positionable against the deformable panel to enclose the space and define the deformable reservoir; wherein manually pressing the blister causes fluid pressure against the foil panel to rupture the foil panel and release the test fluid into the flow path.

In Example 16, the subject matter of Example 15 optionally includes wherein the test cartridge further comprises: a deformable cover comprising at least one reservoir cover, each reservoir cover configured to fit over the deformable reservoir; wherein depressing the reservoir cover deforms and ruptures the deformable reservoir.

In Example 17, the subject matter of any one or more of Examples 11-16 optionally include wherein the sample port is configured to interface with a nozzle of a syringe, the syringe comprising a plunger receivable within a cylinder for receiving biological fluid; wherein depressing the plunger pushes biological fluid into the sample port and through the fluid path.

In Example 18, the subject matter of any one or more of Examples 11-17 optionally include wherein the sensor flow cell defines a waste chamber fluidly connected to the flow path downstream of the testing chamber; wherein fluids displaced from the testing chamber are pushed into the waste chamber.

In Example 19, the subject matter of any one or more of Examples 11-18 optionally include wherein the test cartridge further comprises: a test chip comprising the sensor and at least one reader contact; wherein the test cartridge is configured to be inserted into a reader such that the reader contacts interface with corresponding contacts of the reader.

In Example 20, the subject matter of Example 19 optionally includes wherein the test cartridge further comprises: at least one alignment feature for aligning the reader contacts with the corresponding contacts of the reader.

Example 21 is a method for evaluating a fluid, comprising: providing a test cartridge comprising a sensor flow cell defining a testing chamber and a flow path for passing fluid through the testing chamber, the testing cartridge comprising a sensor positionable within the testing chamber and configured to evaluate fluid within the testing chamber; manually deforming a deformable reservoir that is part of the test cartridge and fluidly connected to the flow path, wherein deformation of the deformable reservoir ruptures the deformable reservoir to release a test fluid into the testing chamber through the flow path; evaluating the test fluid with the sensor to evaluate the sensor; providing a biological fluid into the flow path through a sample port fluidly connected to the flow path downstream of the deformable reservoir and upstream of the testing chamber, wherein the biological fluid displaces the test fluid within the testing chamber; and evaluating the biological fluid with the evaluated sensor.

In Example 22, the subject matter of Example 21 optionally includes wherein the test fluid displaces a storage fluid initially received within the testing chamber.

In Example 23, the subject matter of any one or more of Examples 21-22 optionally include wherein the test fluid comprises a liquid quality control fluid.

In Example 24, the subject matter of Example 23 optionally includes wherein manually deforming a deformable reservoir comprises manually deforming a first deformable reservoir fluidly connected to the flow path, wherein deformation of the deformable reservoir ruptures the first deformable reservoir to release a first test fluid into the testing chamber; and manually deforming a second deformable reservoir fluidly connected to the flow path, wherein deformation of the second deformable reservoir ruptures the second deformable reservoir to release a second test fluid into the testing chamber; wherein the second test fluid displaces the first test fluid within the testing chamber.

In Example 25, the subject matter of any one or more of Examples 21-24 optionally include wherein the sensor is operably connected to a test chip having at least one reader contact.

In Example 26, the subject matter of Example 25 optionally includes interfacing the at least one reader contact with corresponding contacts of a reader to link the sensor with the reader.

Each of these non-limiting examples can stand on its own, or can be combined in any permutation or combination with any one or more of the other examples.

The above detailed description includes references to the accompanying drawings, which form a part of the detailed description. The drawings show, by way of illustration, specific embodiments in which the present subject matter can be practiced. These embodiments are also referred to herein as "examples." Such examples can include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

In the event of inconsistent usages between this document and any documents so incorporated by reference, the usage in this document controls.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In this document, the terms "including" and "in which" are used as the plain-English equivalents of the respective terms "comprising" and "wherein." Also, in the following claims, the terms "including" and "comprising" are open-ended, that is, a system, device, article, composition, formulation, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

Method examples described herein can be machine or computer-implemented at least in part. Some examples can include a computer-readable medium or machine-readable medium encoded with instructions operable to configure an electronic device to perform methods as described in the above examples. An implementation of such methods can include code, such as microcode, assembly language code, a higher-level language code, or the like. Such code can include computer readable instructions for performing various methods. The code may form portions of computer program products. Further, in an example, the code can be tangibly stored on one or more volatile, non-transitory, or non-volatile tangible computer-readable media, such as during execution or at other times. Examples of these tangible computer-readable media can include, but are not limited to, hard disks, removable magnetic disks, removable optical disks (e.g., compact disks and digital video disks), magnetic cassettes, memory cards or sticks, random access memories (RAMs), read only memories (ROMs), and the like.

The above description is intended to be illustrative, and not restrictive. For example, the above-described examples (or one or more aspects thereof) may be used in combination with each other. Other embodiments can be used, such as by one of ordinary skill in the art upon reviewing the above description. The Abstract is provided to comply with 37 C.F.R. § 1.72(b), to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description as examples or embodiments, with each claim standing on its own as a separate embodiment, and it is contemplated that such embodiments can be combined with each other in various combinations or permutations. The scope of the present subject matter should be determined with reference to the appended claims, along with the full scope of equivalents to which such claims are entitled.

What is claimed is:

1. A test cartridge for evaluating a fluid, comprising:
a sensor flow cell defining a testing chamber and a flow path for passing fluid through the testing chamber;
a sensor positionable within the testing chamber and configured to measure a concentration of at least one analyte in a fluid within the testing chamber;
a sample port fluidly connected to the flow path upstream of the testing chamber and configured to receive a biological fluid into the testing chamber through the flow path, wherein the biological fluid has an unknown concentration of the at least one analyte;
first and second deformable reservoirs contained in the cartridge and separate from the sample port, the first deformable reservoir fluidly connected to the flow path upstream of the testing chamber and containing a first liquid control fluid, the second deformable reservoir fluidly connected to the flow path upstream of the testing chamber and containing a second liquid control fluid,
wherein the first and second deformable reservoirs are configured to be sequentially deformed, and manually deforming each deformable reservoir ruptures the deformable reservoir to release the first liquid control fluid and the second liquid control fluid into the testing chamber, and
wherein at least one of the first and second control fluids is a quality control fluid having a known concentration of the at least one analyte:
a reservoir cartridge including a deformable panel and a foil panel, the deformable panel being shaped to form a blister for each deformable reservoir to define a space for receiving a respective one of the first and second liquid control fluids, wherein the foil panel is positionable against the deformable panel to enclose the space and define the first and second deformable reservoirs;
wherein manually pressing the blister for one of the first and second deformable reservoirs causes fluid pressure against the foil panel to rupture the foil panel and release the respective one of the first and second liquid control fluids from the one of the first and second deformable reservoirs into the flow path: and
a deformable cover comprising first and second reservoir covers, the first reservoir cover configured to fit over the first deformable reservoir and the second reservoir cover configured to fit over the second deformable reservoir;
wherein depressing the first or second deformable cover deforms and ruptures a respective one of the first and second deformable reservoirs.

2. The test cartridge of claim 1, wherein the sample port is configured to interface with a nozzle of a syringe, the syringe comprising a plunger receivable within a cylinder for receiving biological fluid;
wherein depressing the plunger pushes biological fluid into the sample port and through the fluid path.

3. The test cartridge of claim 1, wherein the sensor flow cell defines a waste chamber fluidly connected to the flow path downstream of the testing chamber;
wherein fluids displaced from the testing chamber are pushed into the waste chamber.

4. The test cartridge of claim 1, further comprising:
a test chip comprising the sensor and at least one reader contact, wherein the test cartridge is configured to be inserted into a reader such that the at least one reader contact interfaces with corresponding contacts of the reader.

5. A test system for evaluating a fluid, comprising:
a test cartridge, comprising:
a sensor flow cell defining a testing chamber and a flow path for passing fluid through the testing chamber,
a sensor positionable within the testing chamber and configured to measure a concentration of at least one analyte in a test fluid within the testing chamber,
a sample port fluidly connected to the flow path upstream of the testing chamber and configured to receive a biological fluid into the testing chamber through the flow path, wherein the biological fluid has an unknown concentration of the at least one analyte, and
first and second deformable reservoirs contained in the test cartridge and separate from the sample port, the first deformable reservoir fluidly connected to the flow path upstream of the testing chamber and containing a first test fluid, the second deformable reservoir fluidly connected to the flow path upstream of the testing chamber and containing a second test fluid, wherein manually deforming each deformable reservoir sequentially ruptures the deformable reservoir to sequentially release the first test fluid and the second test fluid into the testing chamber, and wherein at least one of the first and second test fluids is a quality control fluid having a known concentration of the at least one analyte;

a reservoir cartridge including a deformable panel and a foil panel, the deformable panel being shaped to form a blister for each deformable reservoir to define a space for receiving a respective one of the first and second test fluids, wherein the foil panel is positionable against the deformable panel to enclose the space and define the first and second deformable reservoirs, wherein manually pressing the blister for one of the first and second deformable reservoirs causes fluid pressure against the foil panel to rupture the foil panel and release the respective one of the first and second test fluids from the one of the first and second deformable reservoirs into the flow path: and a deformable cover comprising first and second reservoir covers, the first reservoir cover configured to fit over the first deformable reservoir and the second reservoir cover configured to fit over the second deformable reservoir;

wherein depressing the first or second deformable cover deforms and ruptures the respective deformable reservoir; and a reader configured to interface with the test cartridge to receive sensor information regarding the concentration of the at least one analyte in the test fluid from the sensor.

6. The test system of claim 5, wherein the sample port is configured to interface with a nozzle of a syringe, the syringe comprising a plunger receivable within a cylinder for receiving biological fluid;

wherein depressing the plunger pushes biological fluid into the sample port and through the fluid path.

7. The test system of claim 5, wherein the sensor flow cell defines a waste chamber fluidly connected to the flow path downstream of the testing chamber;

wherein fluids displaced from the testing chamber are pushed into the waste chamber.

8. The test systemof claim 5, wherein the test cartridge further comprises:

a test chip comprising the sensor and at least one reader contact;

wherein the test cartridge is configured to he inserted into a reader such that the at least one reader contact interfaces with corresponding contacts of the reader.

9. The test system of claim 8, wherein the test cartridge further comprises:

at least one alignment feature for aligning the reader contacts with the corresponding contacts of the reader.

10. A method for evaluating a fluid, comprising:

providing a test cartridge comprising a sensor flow cell defining a testing chamber and a flow path for passing fluid through the testing chamber, the testing cartridge comprising a sensor positionable within the testing chamber and configured to evaluate fluid within the testing chamber;

manually deforming a first deformable reservoir fluidly connected to the flow path wherein deformation of the deformable reservoir ruptures the first deformable reservoir to release a first test fluid into the testing chamber through the flow path; and manually deforming a second deformable reservoir fluidly connected to the flow path, wherein deformation of the second deformable reservoir ruptures the second deformable reservoir to release a second test fluid into the testing chamber through the flow path;

evaluating the test fluid with the sensor to evaluate the sensor;

providing a biological fluid into the flow path through a sample port fluidly connected to the flow path downstream of the deformable reservoir and upstream of the testing chamber, wherein the biological fluid displaces the test fluid within the testing chamber; and evaluating the biological fluid with the evaluated sensor, wherein the second test fluid displaces the first test fluid within the testing chamber, and the first and second test fluids comprise at least one of a liquid quality control fluid for evaluating the sensor and a calibration fluid for calibrating the sensor.

11. The method of claim 10, wherein the sensor is operably connected to a test chip having at least one reader contact.

12. The method of claim 11, further comprising:
interfacing the at least one reader contact with corresponding contacts of a reader to link the sensor with the reader.

* * * * *

UNITED STATES PATENT AND TRADEMARK OFFICE
CERTIFICATE OF CORRECTION

| | |
|---|---|
| PATENT NO. | : 11,235,327 B2 |
| APPLICATION NO. | : 15/947357 |
| DATED | : February 1, 2022 |
| INVENTOR(S) | : Kurkowski et al. |

It is certified that error appears in the above-identified patent and that said Letters Patent is hereby corrected as shown below:

In the Claims

In Column 12, Line 9, in Claim 1, delete "analyte:" and insert --analyte;-- therefor In Column 12, Line 22, in Claim 1, delete "path:" and insert --path;-- therefor In Column 13, Line 12, in Claim 5, delete "reservoirs," and insert --reservoirs;-- therefor In Column 13, Line 18, in Claim 5, delete "path:" and insert --path;-- therefor In Column 13, Line 42, in Claim 8, delete "systemof" and insert --system of-- therefor In Column 14, Line 1, in Claim 8, delete "he" and insert --be-- therefor Signed and Sealed this
Tenth Day of May, 2022

*Katherine Kelly Vidal*

Katherine Kelly Vidal
*Director of the United States Patent and Trademark Office*